United States Patent
Yoshitake et al.

(10) Patent No.: US 7,649,087 B2
(45) Date of Patent: *Jan. 19, 2010

(54) SACCHARIDE RESIDUE-FUNCTIONAL ORGANOPOLYCARBOSILOXANES AND METHOD FOR THE PREPARATION THEREOF

(75) Inventors: Makoto Yoshitake, Chiba (JP); Daiyo Terunuma, Saitama (JP); Koji Matsuoka, Saitama (JP); Ken Hatano, Saitama (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 413 days.

This patent is subject to a terminal disclaimer.

(21) Appl. No.: 10/494,232

(22) PCT Filed: Nov. 12, 2002

(86) PCT No.: PCT/JP02/11806
§ 371 (c)(1),
(2), (4) Date: Oct. 6, 2004

(87) PCT Pub. No.: WO03/042284
PCT Pub. Date: May 22, 2003

(65) Prior Publication Data
US 2005/0043365 A1 Feb. 24, 2005

(30) Foreign Application Priority Data
Nov. 13, 2001 (JP) .............................. 2001-348118

(51) Int. Cl.
*A61K 31/7028* (2006.01)
(52) U.S. Cl. .................. 536/4.1; 536/1.11; 526/238.2; 514/345

(58) Field of Classification Search ................. 536/1.11, 536/4.1; 526/238.2; 528/30; 525/474; 514/345
See application file for complete search history.

(56) References Cited

U.S. PATENT DOCUMENTS
7,208,561 B2 * 4/2007 Yoshitake et al. ............. 528/30

FOREIGN PATENT DOCUMENTS
| EP | 0962482 A1 * | 8/1999 |
| JP | HEI 11-92490 | 8/1989 |
| JP | HEI 5-186596 | 7/1993 |
| JP | SHO 62-68820 | 9/1994 |
| JP | HEI 8-134103 | 5/1996 |
| JP | HEI 10-298288 | 11/1998 |
| JP | HEI11-343347 | 12/1999 |

OTHER PUBLICATIONS
Kuzuhara et al, Tetrahedron Letters, 1999, 40, 7839-7842.*
Roy, Rene, Polymer News, 1996, 21, 226-232.*
Kuzuhara et al, Tet. Lett., 1999, 40, 7839-7842.*
Roy, Polym. News, 1996, 21, 226-232.*

* cited by examiner

Primary Examiner—Shaojia Anna Jiang
Assistant Examiner—Ganapathy Krishnan
(74) Attorney, Agent, or Firm—Howard & Howard Attorneys PLLC

(57) ABSTRACT

A saccharide residue-functional organopolycarbosiloxane containing at least two monosaccharide or polysaccharide groups per molecule in which a specific site on the monosaccharide or polysaccharide is bonded to silicon through a thioether bond. Also, a method of preparing the saccharide residue-functional organopolycarbosiloxane, comprising condensing a saccharide residue-functional metal thiolate compound wherein the metal is an alkali metal atom or alkaline-earth metal atom, and an organopolycarbosiloxane containing groups having the formula —$R^2Q$ wherein $R^2$ is $C_2$ to $C_{10}$ alkylene, and Q is a group selected from halogen atoms, $C_1$ to $C_{10}$ alkylsulfonate groups, and $C_6$ to $C_{20}$ arylsulfonate groups.

9 Claims, No Drawings

SACCHARIDE RESIDUE-FUNCTIONAL ORGANOPOLYCARBOSILOXANES AND METHOD FOR THE PREPARATION THEREOF

This invention relates to novel saccharide residue-functional organopolycarbosiloxanes and to a method for their preparation. More particularly, this invention relates to saccharide residue-functional organopolycarbosiloxanes in which monosaccharide or polysaccharide is bonded at a specific site through a thioether bond to silicon and to a method for the preparation of said saccharide residue-functional organopolycarbosiloxanes.

While the important role played by saccharides in mediating biological functions has been known for some time, unique interactions between substances originating in the steric structure of saccharides have been elucidated only very recently, and, concurrent therewith, the development of drugs and functional materials that effectively utilize these functionalities has attracted attention.

With this goal in mind, methods for bonding saccharides to synthetic polymers are already known, as are attempts to apply these methods. Organosilicon polymers, because they are biologically inert, are ideal materials for drugs, therapeutic materials, and cosmetics, and a number of saccharide residue-functional organopolysiloxanes—and methods for their preparation—have been introduced to date.

For example, Japanese Patent Application Publication (Kokai) No. Sho 62-68820 (68,820/1987) discloses saccharide residue-functional organopolysiloxane in which saccharide is bonded to polysiloxane through an amide bond; Japanese Patent Application Publication (Kokai) No. Hei 5-186596 (186,596/1993) discloses saccharide residue-functional organopolysiloxane in which saccharide is bonded to polysiloxane through a glycosidic bond; Japanese Patent Application Publication (Kokai) No. Hei 8-134103 (134,103/1996) discloses saccharide residue-functional organopolysiloxane in which saccharide is bonded to polysiloxane through a urethane bond; and Japanese Patent Application Publication Hei 11-92490 (92,490/1999) discloses saccharide residue-functional organopolysiloxane in which saccharide is bonded to polysiloxane through a glycosidic or thioglycosidic bond.

There are no reports, however, of the bonding of saccharides to organopolycarbosiloxanes. One would expect that advanced functionality could be imparted to organopolycarbosiloxanes since compounds with special molecular structures, known as dumbbell structures and dendrimer structures, can be produced in this compound class, while such structures are difficult to synthesize in the case of organopolysiloxanes.

The inventors achieved this invention as a result of intensive investigations directed to solving the problems identified above. The objects of this invention relate to novel saccharide residue-functional organopolycarbosiloxanes that can have, for example, a dendrimer or dumbbell-shaped structure and to a method for the preparation of such organopolycarbosiloxanes. More particularly, an object of this invention is to provide a saccharide residue-functional organopolycarbosiloxane in which a specific site on a monosaccharide or polysaccharide is bonded to silicon through a thioether bond. Another object of this invention is to provide a method for the preparation of this saccharide residue-functional organopolycarbosiloxane.

This invention relates to a saccharide residue-functional organopolycarbosiloxane that contains at least two optionally substituted saccharide residues in each molecule and is represented by the general formula:

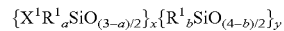

wherein $R^1$ is $C_1$ to $C_{10}$ alkyl or aryl; $X^1$ is a silylalkyl group with the following general formula at i=1:

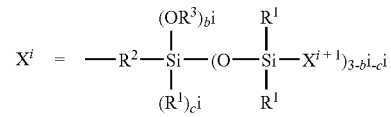

wherein $R^1$ is defined as above, $R^2$ is $C_2$ to $C_{10}$ alkylene, $R^3$ is $C_1$ to $C_{10}$ alkyl, i is an integer from 1 to 10, $b^i$ is an integer from 0 to 3, $c^i$ is an integer from 0 to 3, the sum of $b^i$ and $c^i$ is less than or equal to 3, and $X^{i+1}$ at the point at which i corresponds to the iteration or generation number for the silylalkyl group $X^1$ is a group with the general formula $-R^4-S-R^5-Y$ wherein $R^4$ and $R^5$ are each independently selected from $C_1$ to $C_{20}$ divalent hydrocarbyl and Y is a substituted or unsubstituted, monosaccharide or polysaccharide residue whose bonding site with $R^5$ is an oxygen atom; a is an integer from 0 to 2; b is an integer from 0 to 3; x is an integer with a value of at least 2; and y is an integer with a value of at least 0; wherein when an individual siloxane structural unit is present in a plural number, these may be the same as or may differ from each other.

This invention additionally relates to a method for preparing a saccharide residue-functional organopolycarbosiloxane, which is characterized by effecting a condensation reaction between a saccharide residue-functional metal thiolate compound $M-S-R^5-Y$ wherein $R^5$ and Y are defined as above, M is an alkali metal atom or alkaline-earth metal atom, and an organopolycarbosiloxane represented by the general formula:

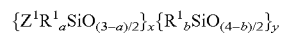

wherein $R^1$, a, b, x, and y are defined as above and $Z^1$ is a silylalkyl group with the following general formula at i=1:

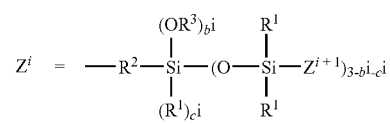

wherein $R^1$, $R^2$, $R^3$, $b^i$, and $c^i$ are defined as above and $Z^{i+1}$ at the point at which i corresponds to the iteration or generation number for the silylalkyl group $Z^1$ is a group with the general formula $-R^2Q$ in which $R^2$ is defined as above and Q is a group selected from halogen atoms, $C_1$ to $C_{10}$ alkylsulfonate groups, and $C_6$ to $C_{20}$ arylsulfonate groups wherein at least two Q groups are present in each molecule of the organopolycarbosiloxane.

The saccharide residue-functional organopolycarbosiloxane according to this invention is represented by the following general formula:

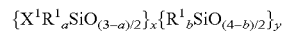

$R^1$ in this formula is $C_1$ to $C_{10}$ alkyl or aryl. Alkyl can be exemplified by methyl, ethyl, propyl, butyl, pentyl, isopropyl, isobutyl, cyclopentyl, and cyclohexyl, while aryl can be exemplified by phenyl and naphthyl. Methyl is preferred among the preceding for $R^1$. $X^1$ in the preceding general formula is a silylalkyl group with the following general formula at i=1:

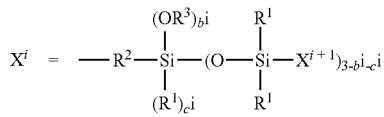

and is bonded to the silicon atom in the organopolycarbosiloxane.

$R^1$ in this formula is defined as above, while $R^2$ is $C_2$ to $C_{10}$ alkylene, which can be exemplified by straight-chain alkylene such as ethylene, propylene, butylene, and hexylene and by branched alkylene such as methylmethylene, methylethylene, 1-methylpentylene, and 1,4-dimethylbutylene. Preferred among the preceding are ethylene, methylmethylene, hexylene, 1-methylpentylene, and 1,4-dimethylbutylene. $R^3$ is $C_1$ to $C_{10}$ alkyl and can be exemplified by methyl, ethyl, propyl, butyl, pentyl, and isopropyl, among which methyl and ethyl are preferred. i is an integer from 1 to 10, $b^i$ is an integer from 0 to 3, $c^i$ is an integer from 0 to 3, and the sum of $b^i$ and $c^i$ is less than or equal to 3. $X^{i+1}$ at the point at which i corresponds to the iteration or generation number for the silylalkyl group $X^1$ is a group with the general formula —$R^4$—S—$R^5$—Y.

The inventive organopolycarbosiloxane must contain at least two saccharide residues in each molecule. This is because the manifestation of unique properties not accessible by a single saccharide residue as well as enhancements in the effective activity can be expected from interactions between or among a plurality of saccharide residues present in the molecule.

As used herein, the iteration number of the silylalkyl group denotes the number of repeat units with the general formula:

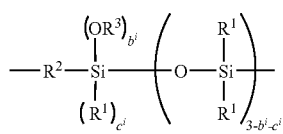

wherein $R^1$, $R^2$, $R^3$, $b^i$, and $c^i$ are defined as above in the subject silylalkyl group when the silylalkyl group has a straight-chain molecular structure. The generation number of the silylalkyl group denotes the number of levels in the subject silylalkyl group when the silylalkyl group has a branched molecular structure, wherein a level is composed of a molecular structural unit with the general formula:

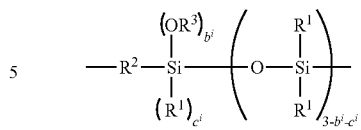

wherein $R^1$, $R^2$, $R^3$, $b^i$, and $c^i$ are defined as above.

Therefore, letting $R^6$ represent the group with the general formula —$R^4$—S—$R^5$—Y, $X^1$ then has the following general formula when the iteration or generation number for the silylalkyl group is 1:

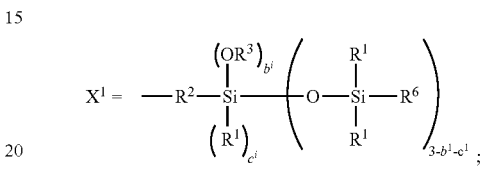

$X^1$ has the following general formula when the iteration or generation number for the silylalkyl group is 2:

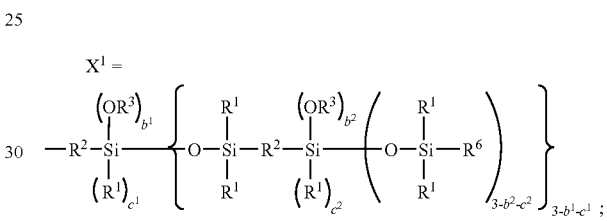

and $X^1$ has the following general formula when the iteration or generation number for the silylalkyl group is 3:

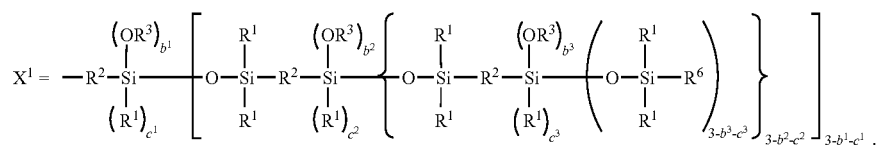

$R^4$ and $R^5$ in $R^6$ each independently represent $C_1$ to $C_{20}$ divalent hydrocarbyl and can be exemplified by straight-chain alkylene such as ethylene, propylene, butylene, and hexylene; branched alkylene such as methylmethylene, methylethylene, 1-methylpentylene, and 1,4-dimethylbutylene; arylene such as 1,4-phenylene, 1,3-phenylene, and 4,4'-biphenylene; and aralkylene such as 1,4-bis(methylene)phenylene and 2,2-(para-phenylene)propylene. Y in $R^6$ represents a substituted or unsubstituted, monosaccharide or polysaccharide residue whose bonding site with $R^5$ is in all instances an oxygen atom.

Monosaccharide units that can form the saccharide residue can be exemplified by glucopyranose (glucose), mannose, allose, altrose, galactose, idose, talose, gulose, ribose, arabinose, xylose, fructose, fucose, N-acetylglucosamine, N-acetylgalactosamine, sialic acid, and esters of the preceding. Y can be specifically exemplified by monosaccharide residues such as glucopyranosyl (glucosyl), mannosyl, allosyl, altrosyl, galactosyl, idosyl, talosyl, gulosyl, ribosyl, arabinosyl, xylosyl, fucosyl, fructosyl, N-acetylglucosaminyl, N-acetylgalactosaminyl, sialyl, and their esters; oligosaccharide residues such as maltosyl, cellobiosyl, lactosyl, mannotriosyl, globotriosyl, and their esters; and polysaccharide residues such as cellulosyl and amylosyl and their esters. Preferred among the preceding are monosaccharide residues and oligosaccharide residues that contain no more than 5 saccharide units. Moreover, the oxygen atom in Y that bonds with $R^5$ is preferably a glycosidic oxygen atom. $R^6$ can be specifically exemplified by structures having the following chemical formulas, wherein Ac is acetyl:

The subscripts in the general formula $\{X^1R^1{}_a SiO_{(3-a)/2}\}_x\{R^1{}_b SiO_{(4-b)/2}\}_y$ that represents the inventive saccharide residue-functional organopolycarbosiloxane have the following values: a is an integer from 0 to 2, b is an integer from 0 to 3, x is an integer with a value of at least 2, and y is an integer with a value of at least 0. When an individual siloxane structural unit is present in a plural number, these may be the same as or may differ from each other.

The organopolycarbosiloxane under consideration can be specifically exemplified by organopolycarbosiloxanes with

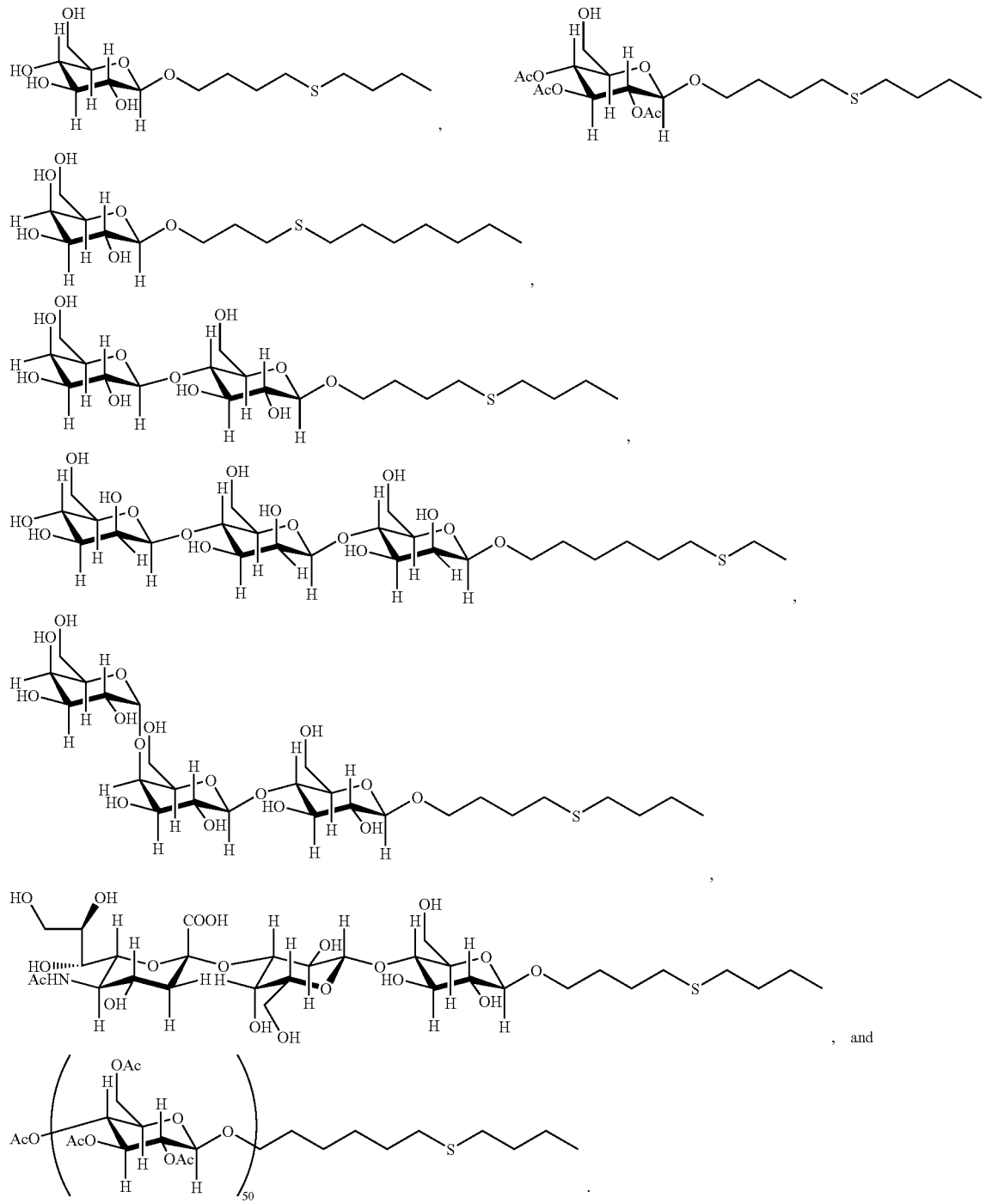

the following general formulas, in which $X^1$ and $R^1$ are defined as above and e, f, g, h, j, k, l, m, and n are integers that indicate the number of siloxane units present in each molecule:

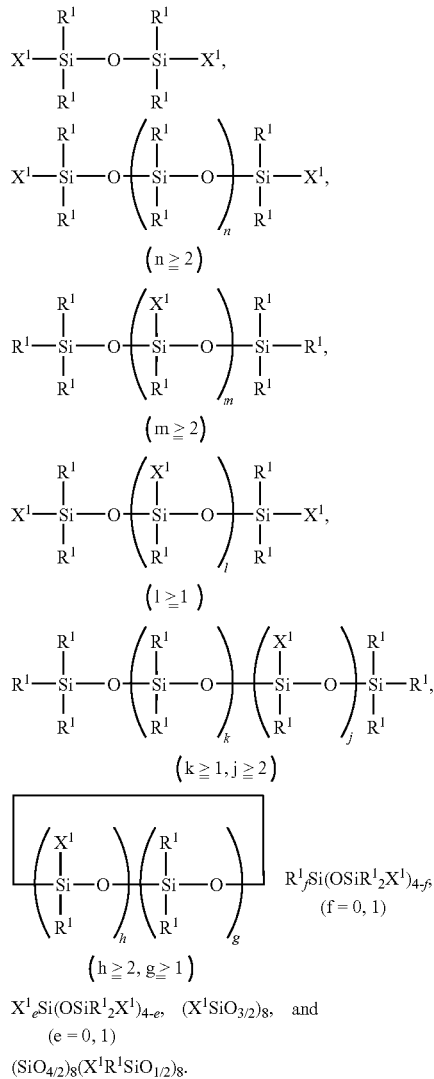

$X^1_e Si(OSiR^1_2 X^1)_{4-e}$, $(X^1 SiO_{3/2})_8$, and
(e = 0, 1)
$(SiO_{4/2})_8 (X^1 R^1 SiO_{1/2})_8$.

The inventive saccharide residue-functional organopolycarbosiloxane can be synthesized by effecting a condensation reaction between a saccharide residue-functional metal thiolate compound M—S—$R^5$—Y and an organopolycarbosiloxane represented by the general formula $\{Z^1 R^1_a SiO_{(3-a)/2}\}_x \{R^1_b SiO_{(4-b)/2}\}_y$, wherein $R^1$, $R^2$, a, b, x, and y are defined as above and $Z^1$ is a silylalkyl group with the following general formula at i=1:

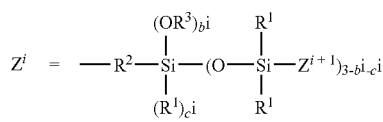

and is bonded to a silicon atom in the organopolycarbosiloxane. $R^1$, $R^2$, $R^3$, $b^i$, and $c^i$ in this general formula are defined as above. $Z^{i+1}$ at the point at which i corresponds to the iteration or generation number of the silylalkyl group is a group with the general formula —$R^2 Q$ in which $R^2$ is defined as above and Q is a group selected from halogen atoms, $C_1$ to $C_{10}$ alkylsulfonate groups, and $C_6$ to $C_{20}$ arylsulfonate groups.

The halogen atoms encompassed by Q can be exemplified by the chlorine atom, bromine atom, and iodine atom. The alkylsulfonate group can be exemplified by methanesulfonate and ethanesulfonate and the arylsulfonate group can be exemplified by benzenesulfonate and toluenesulfonate.

$R^5$ and Y in the saccharide residue-functional metal thiolate compound M—S—$R^5$—Y retain their definitions from above, while M is an alkali metal or alkaline-earth metal atom, for example, lithium, sodium, potassium, calcium, or magnesium. Since saccharide residue-functional metal thiolate compounds M—S—$R^5$—Y are generally difficult to isolate, the product synthesized in the reaction system, for example, by the action of a metal or metal hydride on the corresponding saccharide residue-functional thiol compound or by the action of a metal on the corresponding saccharide residue-functional thioester or thioether compound, is preferably used directly for the condensation reaction.

The organopolycarbosiloxane starting material $\{Z^1 R^1_a SiO_{(3-a)/2}\}_x \{R^1_b SiO_{(4-b)/2}\}_y$ used in the synthesis of the inventive saccharide residue-functional organopolycarbosiloxane can itself be synthesized by known methods, and the particular method used is not critical. For example, this starting material can be directly synthesized by a hydrosilylation reaction between a halogen-, alkylsulfonate-, or arylsulfonate-functional alkenyl compound and carbosiloxane dendrimer bearing silicon-bonded hydrogen at its branch ends as synthesized by the methods taught in Japanese Patent Application Publication (Kokai) No. Hei 10-298288 (298,288/1998) and Japanese Patent Application Publication (Kokai) No. Hei 11-343347 (343,347/1999). Alternatively, the hydroxyl group can be introduced at the branch ends of the above-referenced carbosiloxane dendrimer and, utilizing this hydroxyl, halogen can then be introduced by a substitution reaction while alkylsulfonate or arylsulfonate can be introduced by an esterification reaction.

The saccharide residue-functional metal thiolate compound M—S—$R^5$—Y can be synthesized, for example, by converting the glycosidic hydroxyl of the saccharide molecule to an alkenyl ether by a known method; addition reacting a thiocarboxylic acid or thiol compound with the alkenyl group in the presence of a radical initiator to give, respectively, a thioester derivative or thioether compound; and reacting these products, respectively, with an alkali metal base such as alkali metal hydroxide or alkali metal methoxide, with alkaline-earth metal base such as alkaline-earth metal hydroxide, with an alkali metal, or with alkaline-earth metal.

The inventive saccharide residue-functional organopolycarbosiloxane as described hereinabove has a number of characteristic features. For example, it bears saccharide residues in a configuration in which a specific site on the monosaccharide or polysaccharide is bonded to silicon through a thioether bond. As another characteristic feature, the inventive saccharide residue-functional organopolycarbosiloxane can have a variety of molecular structures ranging from straight-chain molecular structures to dendrimer structures that contain a large number of branch structures.

As a consequence, due to interactions between or among the saccharide residues in the molecule, this organopolycarbosiloxane can manifest, in addition to the properties inherently possessed by saccharides such as pharmacological activity and biocompatibility, unique properties not accessible by a single saccharide residue as well as enhancements in the effective activity or activities. The inventive organopolycarbosiloxane therefore has the advantage of being useful in various applications, for example, as an ingredient for cosmetics, as a reagent for the separation of optical isomers, as a therapeutic material for the separation of, for example, toxins or viruses, as a therapeutic agent, and as an agrochemical. The inventive method for synthesizing a saccharide residue-functional organopolycarbosiloxane is characterized by its ability to very efficiently produce the subject organopolycarbosiloxane.

ldimethylsiloxy)silylpropyldimethysiloxy}silane, from which the trimethylsiloxy group was subsequently eliminated by the action of excess methanol to give tetrakis{tris(hydroxypropyldimethylsiloxy)silylpropyldimethyl-siloxy}silane. Methanesulfonyl chloride was then reacted in pyridine with the tetrakis{tris(hydroxypropyldimethylsiloxy)silylpropyldimethylsiloxy}silane to give tetrakis{tris(methanesulfonyloxypropyldimethylsiloxy)silylpropyldimethylsiloxy}silane, which was subsequently reacted with sodium bromide in DMF to give tetrakis{tris(bromo-propyldimethylsiloxy)silylpropyldimethylsiloxy}silane:

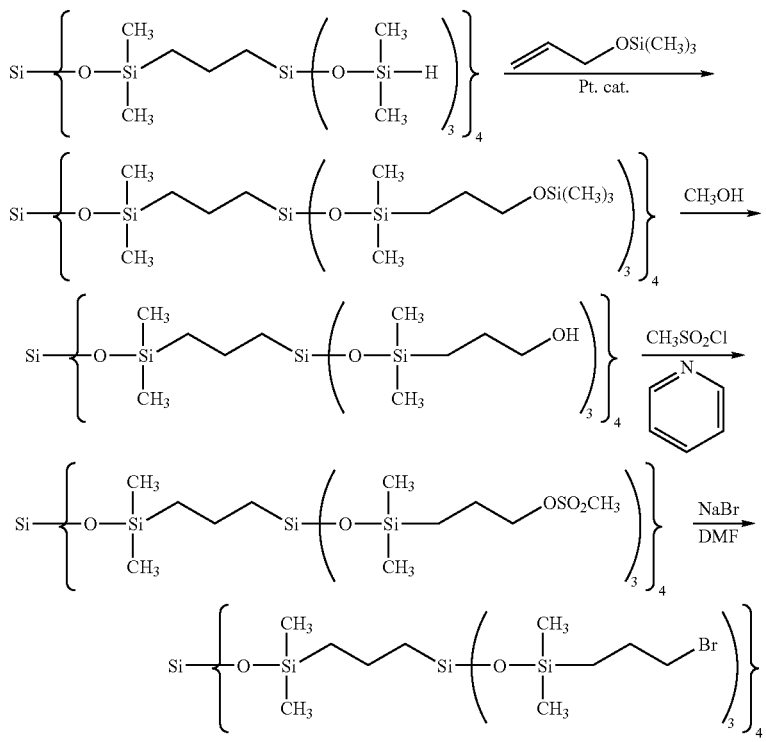

The invention is explained in greater detail hereinbelow through working examples. The inventive saccharide residue-functional organopolycarbosiloxane was identified in the examples by nuclear magnetic resonance analysis. In the reaction equations, chemical formulas, and text that follow, Pt cat. denotes a complex of platinum and 1,1,3,3-tetramethyl-1,3-divinyldisiloxane, Ac stands for the acetyl group, DMF stands for N,N-dimethylformamide, AIBN stands for azobisisobutyronitrile, and Ph stands for the phenyl group.

REFERENCE EXAMPLE 1

Tetrakis{tris(bromopropyldimethylsiloxy)silylpropyldimethylsiloxy}silane was synthesized by the following reactions starting from tetrakis{tris(dimethylsiloxy)silylpropyldimethylsiloxy}silane that had been produced by the method described in Japanese Patent Application Publication (Kokai) No. Hei 10-298288. Thus, allyloxytrimethylsilane was reacted with tetrakis{tris(dimethylsiloxy)silylpropyldimethylsiloxy}silane in the presence of a platinum 1,1,3,3-tetramethyl-1,3-divinyldisiloxane complex as catalyst to produce tetrakis{tris(trimethylsiloxypropy-

REFERENCE EXAMPLE 2

Methyltris{tris(bromopropyldimethylsiloxy)silylpropyldimethylsiloxy}silane was synthesized by the following reactions starting from methyltris{tris(dimethylsiloxy)-silylpropyly dimethylsiloxy}silane that had been produced by the method described in Japanese Patent Application Publication (Kokai) No. Hei 10-298288. Thus, allyloxytrimethylsilane was reacted with methyltris{tris(dimethylsiloxy)silylpropyl-dimethylsiloxy}silane in the presence of a platinum 1,1,3,3-tetramethyl-1,3-divinyldisiloxane complex as catalyst to produce methyltris{tris(trimethylsiloxypropyl-dimethylsiloxy)silylpropyldimethylsiloxy}silane, from which the trimethylsiloxy group was subsequently eliminated by the action of excess methanol to give methyltris{tris(hydroxy-propyldimethylsiloxy)silylpropyldimethylsiloxy}silane.

Methanesulfonyl chloride was then reacted in pyridine with the methyltris{tris-(hydroxypropyldimethylsiloxy)silylpropyldimethylsiloxy}silane to give methyltris{tris-(methanesulfonyloxypropyldimethylsiloxy)silylpropyldimethylsiloxy}silane, which was subsequently reacted with sodium bromide in DMF to give methyltris{tris(bromo-propyldimethylsiloxy)silylpropyldimethylsiloxy}silane:

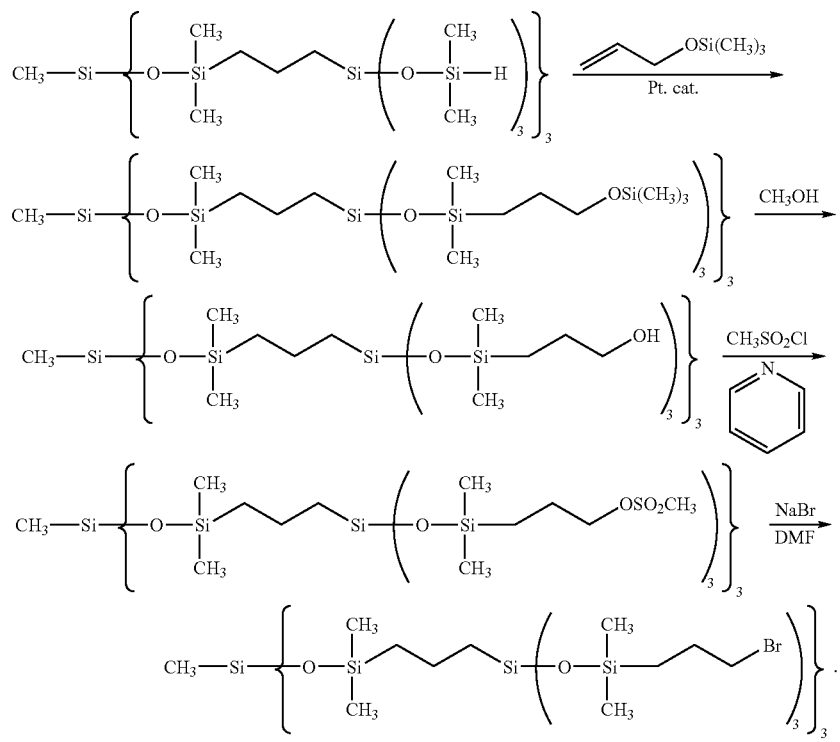

REFERENCE EXAMPLE 3

4-acetylthiobutyl 2,3,4,6-tetra-O-acetyl-β-D-glucopyranoside was synthesized by the following reactions from β-D-glucopyranose. Thus, acetyl 2,3,4,6-tetra-O-acetyl-β-D-glucopyranoside was prepared by exhaustive acetylation of the hydroxyl groups in β-D-glucopyranose by the action of sodium acetate in acetic anhydride. The acetyl 2,3,4,6-tetra-O-acetyl-β-D-glucopyranoside was subsequently reacted with 3-buten-1-ol under catalysis by boron trifluoride diethyl etherate to give butenyl 2,3,4,6-tetra-O-acetyl-β-D-glucopyranoside. The butenyl 2,3,4,6-tetra-O-acetyl-β-D-glucopyranoside was mixed with thioacetic acid in dioxane and AIBN was added as radical initiator; reaction then gave 4-acetylthiobutyl 2,3,4,6-tetra-O-acetyl-β-D-glucopyranoside:

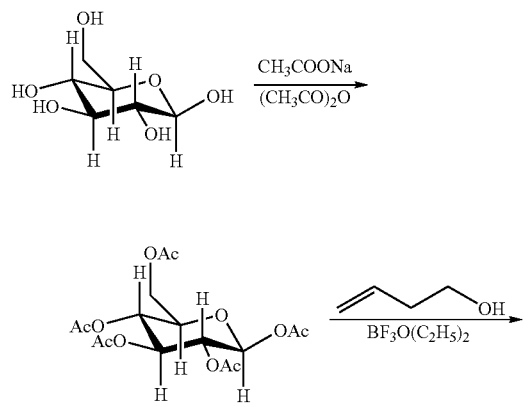

-continued

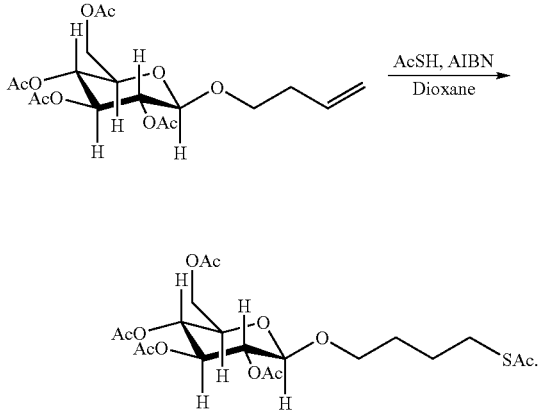

REFERENCE EXAMPLE 4

4-benzylthiobutyl β-D-glucopyranoside was synthesized by the following reactions from β-D-glucopyranose. Thus, acetyl 2,3,4,6-tetra-O-acetyl-β-D-glucopyranoside was prepared by exhaustive acetylation of the hydroxyl groups in β-D-glucopyranose by the action of sodium acetate in acetic anhydride. The acetyl 2,3,4,6-tetra-O-acetyl-β-D-glucopyranoside was subsequently reacted with 3-buten-1-ol under catalysis by boron trifluoride diethyl etherate to give butenyl 2,3,4,6-tetra-O-acetyl-β-D-glucopyranoside. The butenyl 2,3,4,6-tetra-O-acetyl-β-D-glucopyranoside was mixed with benzyl thiol in dioxane and AIBN was added as radical initiator; reaction then gave 4-benzylthiobutyl 2,3,4,6-tetra-O-acetyl-β-D-glucopyranoside. Deacetylation of the 4-benzylthiobutyl 2,3,4,6-tetra-O-acetyl-β-D-glucopyranoside by reaction with sodium methoxide in methanol gave 4-benzylthiobutyl β-D-glucopyranoside:

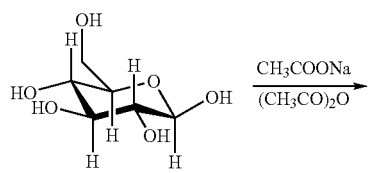

4-acetylthiobutyl 2,3,4,6-tetra-O-acetyl-β-D-glucopyranoside synthesized in Reference Example 3 were dissolved in 0.5 mL anhydrous DMF and 0.5 mL anhydrous methanol, and the liquid mixture was stirred for 2 hours at room temperature. Sodium methoxide (62 mg, 1.12 mmol) was then added and stirring was carried out for another 24 hours at 35° C. Acetic acid (0.5 mL) was added, stirring was carried out for 10 minutes at room temperature, and the reaction solution was then concentrated in vacuo. Acetic anhydride (5 mL) and 5 mL pyridine were added with mixing, the reaction solution was subsequently poured into ice water, and the resulting mixture was extracted 3 times with chloroform.

The combined organic layers were washed with 1 N hydrochloric acid, saturated aqueous sodium bicarbonate, saturated aqueous sodium chloride, and then dried over anhydrous magnesium sulfate. After concentration, the product was purified by column chromatography and gel permeation chromatography to give 95 mg of a saccharide residue-functional organopolycarbosiloxane with the following formula:

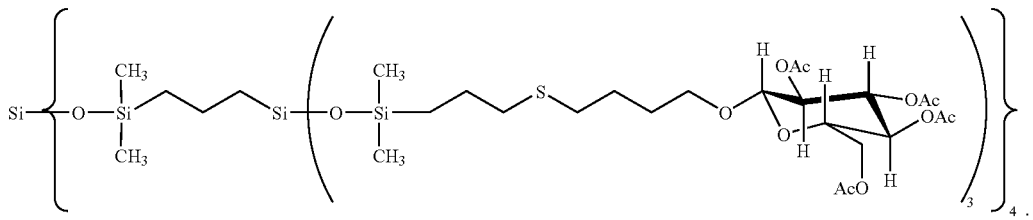

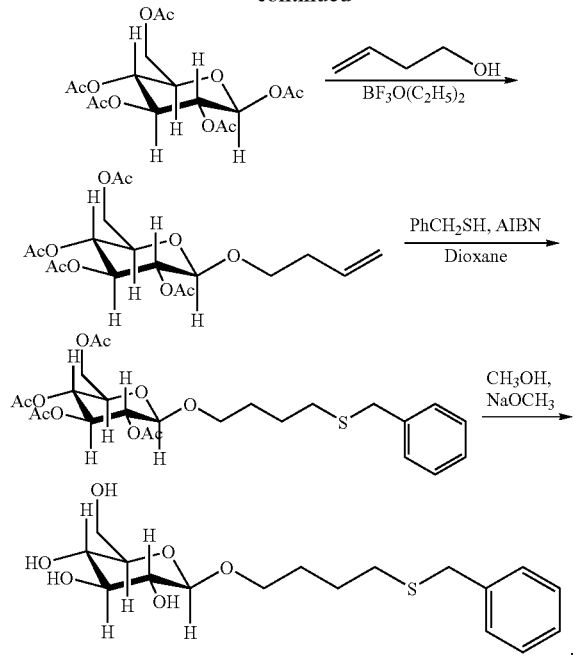

EXAMPLE 1

The tetrakis{tris(bromopropyldimethylsiloxy)silylpropyldimethyl siloxy}silane synthesized in Reference Example 1 (81 mg, 275 mmol) and 474 mg (0.990 mmol) of the

[1]H-nuclear magnetic resonance spectral data (solvent: deuterochloroform) δ=0.06 (bs, 96H), 0.09 (s, 54H), 0.48 (t, J=9 Hz, 9H), 0.63 (t, J=9 Hz, 32H), 1.33 (m, 9H), 1.5-1.7 (m, 72H), 2.00 (s, 36H), 2.02 (s, 36H), 2.04 (s, 36H), 2.08 (s, 36H), 2.50 (t, J=6 Hz, 48H), 3.5 (m, 12H), 3.7 (m, 12H), 4.1 (m, 12H), 4.20 (m, 12H), 4.27 (m, 12H), 4.50 (d, J=8 Hz, 12H), 4.97 (t, J=10 Hz, 12H), 5.07 (t, J=10 Hz, 12H), 5.17 (t, J=10 Hz, 12H).

EXAMPLE 2

The methyltris{tris(bromopropyldimethylsiloxy)silylpropyldimethylsiloxy}silane synthesized in Reference Example 2 (70 mg, 0.0312 mmol) and 404 mg (0.843 mmol) of the 4-acetylthiobutyl 2,3,4,6-tetra-O-acetyl-β-D-glucopyranoside synthesized in Reference Example 3 were dissolved in 0.5 mL anhydrous DMF and 0.5 mL anhydrous methanol, and the liquid mixture was stirred for 2 hours at room temperature. Sodium methoxide (51 mg, 0.928 mmol) was then added and stirring was carried out for another 24 hours at 35° C. Acetic acid (0.4 mL) was added, stirring was carried out for 10 minutes at room temperature, and the reaction solution was then concentrated in vacuo. Acetic anhydride (5 mL) and 5 mL pyridine were added with mixing, the reaction solution was subsequently poured into ice water, and the resulting mixture was extracted 3 times with chloroform.

The combined organic layers were washed with 1 N hydrochloric acid, saturated aqueous sodium bicarbonate, saturated aqueous sodium chloride, and then dried over anhydrous magnesium sulfate. After concentration, the product was purified by column chromatography and gel permeation chromatography to give 125 mg of a saccharide residue-functional organopolycarbosiloxane with the following formula:

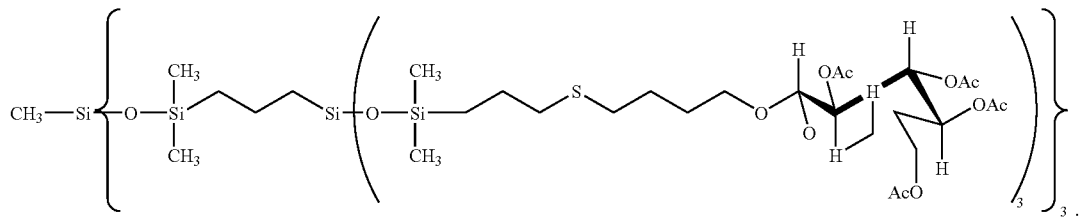

$^1$H-nuclear magnetic resonance spectral data (solvent: deuterochloroform) δ=0.06 (s, 3H), 0.07 (s, 18H), 0.09 (s, 54H), 0.48 (t, J=9 Hz, 6H), 0.63 (t, J=9 Hz, 24H), 1.33 (m, 6H), 1.5-1.7 (m, 54H), 2.00 (s, 27H), 2.02 (s, 27H), 2.04 (s, 27H), 2.08 (s, 27H), 2.50 (t J=6 Hz, 36H), 3.5 (m, 9H), 3.7 (m, 9H), 4.1 (m, 9H), 4.20 (m, 9H), 4.27 (m, 9H), 4.50 (d, J=8 Hz, 9H), 4.97 (t, J=10 Hz, 9H), 5.07 (t, J=10 Hz, 9H), 5.17 (t, J=10 Hz, 9H).

EXAMPLE 3

The 4-benzylthiobutyl β-D-glucopyranoside synthesized in Reference Example 4 (353 mg, 0.985 mmol) was cooled to −35° C., ammonia gas was bubbled in so as to liquefy 30 mL ammonia, 226 mg (9.85 mmol) sodium metal was added, and stirring was carried out for 30 minutes at −35° C. This was followed by the addition of 474 mg (8.86 mmol) ammonium chloride and 92 mg (0.041 mmol) of the methyltris{tris(bromopropyldimethylsiloxy)-silylpropyl dimethylsiloxy}silane synthesized in Reference Example 2 dissolved in 3 mL dimethoxyethane, and while stirring the temperature was then gradually returned to room temperature with evaporation of ammonia gas. After concentration, the product was purified by column chromatography and gel permeation chromatography to give 16 mg of a saccharide residue-functional organopolycarbosiloxane with the following formula:

X is a silylalkyl group having the formula at i=1:

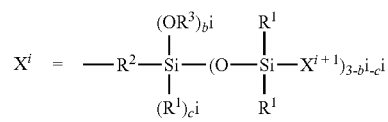

wherein
$R^1$ is $C_1$ to $C_{10}$ alkyl or aryl,
$R^2$ is $C_2$ to $C_{10}$ alkylene,
$R^3$ is $C_1$ to $C_{10}$ alkyl,
i represents an iteration or generation number and is an integer from 1 to 10,
$b^i$ is an integer from 0 to 3,
$c^i$ is an integer from 0 to 3,
the sum of $b^i$ and $c^i$ is less than or equal to 3, and
$X^{i+1}$ at the point at which i corresponds to the iteration or generation number for the silylalkyl group X is a group with the general formula

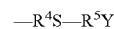

wherein
$R^4$ and $R^5$ are each independently selected from $C_1$ to $C_{20}$ divalent hydrocarbyl, and

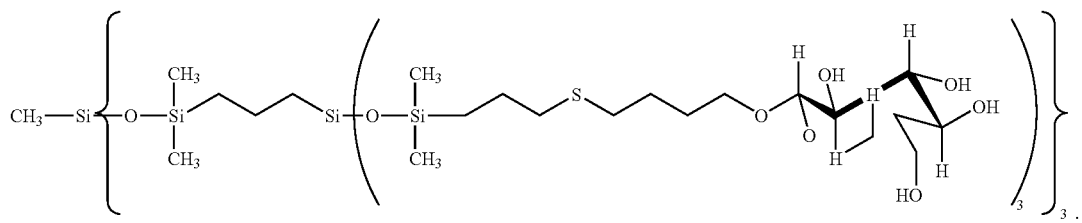

$^1$H-nuclear magnetic resonance spectral data (solvent: deuterium oxide) δ=0.0 (bs, 75H), 0.5 (t, J=9 Hz, 6H), 0.6 (m, 24H), 1.3-1.8 (m, 60H), 2.5 (m, 36H), 3.1 (m, 9H), 3.2-3.4 (m, 27H), 3.5-3.6 (m, 18H), 3.8 (m, 18H), 4.3 (bd, 9H).

What is claimed is:

1. A saccharide residue-functional organopolycarbosiloxane having the formula:

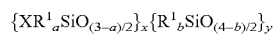

wherein
$R^1$ is $C_1$ to $C_{10}$ alkyl or aryl;
a is an integer from 0 to 2;
b is an integer from 0 to 3;
x is an integer with a value of at least 2;
y is an integer with a value of at least 0; and Y is selected from the group consisting of a substituted monosaccharide, substituted polysaccharide, unsubstituted monosaccharide and unsubstituted polysaccharide residues having an oxygen atom bonded to $R^5$;

provided the organopolycarbosiloxane contains at least two saccharide groups per molecule.

2. The saccharide residue-functional organopolycarbosiloxane according to claim 1, wherein $R^1$ is methyl.

3. The saccharide residue-functional organopolycarbosiloxane according to claim 1, wherein $R^2$ is selected from ethylene, methylmethylene, hexylene, 1-methylpentylene, and 1,4-dimethylbutylene.

4. The saccharide residue-functional organopolycarbosiloxane according to claim 1, wherein $R^3$ is selected from the group consisting of methyl or ethyl.

5. The saccharide residue-functional organopolycarbosiloxane according to claim 1, wherein Y is a monosaccharide residue.

6. The saccharide residue-functional organopolycarbosiloxane according to claim 1, wherein Y is an oligosaccharide residue containing no more than five saccharide units.

7. The saccharide residue-functional organopolycarbosiloxane according to claim 1, wherein the oxygen atom in Y bonded to $R^5$ is a glycosidic oxygen atom.

8. A method of preparing a saccharide residue-functional organopolycarbosiloxane, having the formula:

$$\{XR^1{}_aSiO_{(3-a)/2}\}_x\{R^1{}_bSiO_{(4-b)/2}\}_y$$

wherein
$R^1$ is $C_1$ to $C_{10}$ alkyl or aryl;
a is an integer from 0 to 2;
b is an integer from 0 to 3;
x is an integer with a value of at least 2;
y is an integer with a value of at least 0; and
X is a silylalkyl group having the formula at i=1:

$$X^i = -R^2-\underset{(R^1)_{ci}}{\underset{|}{\overset{(OR^3)_{bi}}{\overset{|}{Si}}}}-(O-\underset{R^1}{\underset{|}{\overset{R^1}{\overset{|}{Si}}}}-X^{i+1})_{3-b^i-c^i}$$

wherein
i represents an iteration or generation number and is an integer from 1 to 10,
$R^1$ is $C_1$ to $C_{10}$ alkyl or aryl,
$R^2$ is $C_2$ to $C_{10}$ alkylene,
$R^3$ is $C_1$ to $C_{10}$ alkyl,
$b^i$ is an integer from 0 to 3,
$c^i$ is an integer from 0 to 3,
the sum of $b^i$ and $c^i$ is less than or equal to 3, and
$X^{i+1}$ at the point at which i corresponds to the iteration or generation number for the silylalkyl group X is a group with the general formula

—$R^4$—S—$R^5$Y wherein
$R^4$ and $R^5$ are each independently selected from $C_1$ to $C_{20}$ divalent hydrocarbyl, and
Y is selected from the group consisting of a substituted monosaccharide, unsubstituted monosaccharide, substituted polysaccharide, and unsubstituted polysaccharide residues having an oxygen atom bonded to $R^5$; said method comprising condensing:
a saccharide residue functional metal thiolate compound having the formula

M-S—$R^5$—Y wherein
$R^5$ is C1 to C20 divalent hydrocarbyl,
Y is a substituted or unsubstituted monosaccharide or polysaccharide residue having an oxygen atom bonded to R5, and
M is an alkali metal atom or alkaline earth metal atom, and an organopolycarbosiloxane having the formula:

$$\{ZR^1{}_aSiO_{(3-a)/2}\}_x\{R^1{}_bSiO_{(4-b)/2}\}_y$$

wherein
$R^1$ is $C_1$ to $C_{10}$ alkyl or aryl;
a is an integer from 0 to 2;
b is an integer from 0 to 3;
x is an integer with a value of at least 2;
y is an integer with a value of at least 0; and Z is a silylalkyl group having the formula at i=1:

$$Z^i = -R^2-\underset{(R^1)_{ci}}{\underset{|}{\overset{(OR^3)_{bi}}{\overset{|}{Si}}}}-(O-\underset{R^1}{\underset{|}{\overset{R^1}{\overset{|}{Si}}}}-Z^{i+1})_{3-b^i-c^i}$$

wherein
$R^1$ is $C_1$ to $C_{10}$ alkyl or aryl,
R is $C_2$ to $C_{10}$ alkylene,
$R^3$ is $C_1$ to $C_{10}$ alkyl,
i represents an iteration or generation number and is an integer from 1 to 10,
$b^i$ is an integer from 0 to 3,
$c^i$ is an integer from 0 to 3,
the sum of $b^i$ and $c^i$ is less than or equal to 3, and
$Z^{i+1}$ at the point at which i corresponds to the iteration or generation number for the silylalkyl group Z is a group having the formula

—$R^2$Q wherein
$R^2$ is defined as above,
Q is a group selected from the group consisting of halogen atoms,
$C_1$ to $C_{10}$ alkylsulfonate groups, and
$C_6$ to $C_{20}$ arylsulfonate groups;
provided the organopolycarbosiloxane contains at least two Q groups per molecule.

9. The saccharide residue-functional organopolycarbosiloxane according to claim 1 having the formula:

$$\{XR^1{}_2SiO_{(1/2)}\}_3\{SiO_{4/2}\}$$

wherein X has the following general formula when i=2:

$$X^i = -R^2-\underset{(R^1)_{c^1}}{\underset{|}{\overset{(OR^3)_{b^1}}{\overset{|}{Si}}}}\left\{O-\underset{R^1}{\underset{|}{\overset{R^1}{\overset{|}{Si}}}}-R^2-\underset{(R^1)_{c^2}}{\underset{|}{\overset{(OR^3)_{b^2}}{\overset{|}{Si}}}}\left(O-\underset{R^1}{\underset{|}{\overset{R^1}{\overset{|}{Si}}}}-R^6\right)_{3-b^2-c^2}\right\}_{3-b^1-c^1}$$

wherein $R^6$ represents the group with the general formula —$R^4$S—$R^5$Y.

* * * * *

UNITED STATES PATENT AND TRADEMARK OFFICE
CERTIFICATE OF CORRECTION

PATENT NO. : 7,649,087 B2  
APPLICATION NO. : 10/494232  
DATED : January 19, 2010  
INVENTOR(S) : Makoto Yoshitake et al.

It is certified that error appears in the above-identified patent and that said Letters Patent is hereby corrected as shown below:

Column 18, line 50-55, in claim 9, delete the subscript [$3\text{-}b^1\text{-}c^2$] and insert therein -- $3\text{-}b^1\text{-}c^1$ --.

Signed and Sealed this

Twenty-third Day of November, 2010

David J. Kappos  
*Director of the United States Patent and Trademark Office*

UNITED STATES PATENT AND TRADEMARK OFFICE
CERTIFICATE OF CORRECTION

PATENT NO.        : 7,649,087 B2
APPLICATION NO.   : 10/494232
DATED             : January 19, 2010
INVENTOR(S)       : Yoshitake et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this

Twenty-first Day of December, 2010

David J. Kappos
*Director of the United States Patent and Trademark Office*